United States Patent
Lai et al.

(10) Patent No.: US 6,595,058 B2
(45) Date of Patent: Jul. 22, 2003

(54) METHOD AND APPARATUS FOR DETERMINING DYNAMIC RESPONSE OF MICROSTRUCTURE BY USING PULSED BROAD BANDWIDTH ULTRASONIC TRANSDUCER AS BAW HAMMER

(75) Inventors: Wen Pin Lai, Taipei (TW); Weileun Fang, Hsinchu (TW)

(73) Assignee: Computed Ultrasound Global Inc., Hsinchu (TW)

( * ) Notice: Subject to any disclaimer, the term of this patent is extended or adjusted under 35 U.S.C. 154(b) by 36 days.

(21) Appl. No.: 09/884,273

(22) Filed: Jun. 19, 2001

(65) Prior Publication Data

US 2002/0189357 A1 Dec. 19, 2002

(51) Int. Cl.[7] .................. G01N 29/00; H01L 41/00; G01M 7/00
(52) U.S. Cl. .............. 73/584; 73/651; 73/662; 310/334
(58) Field of Search .............. 73/584, 655, 662, 73/649, 650, 651, 658, 663; 310/334, 336, 338, 357, 358, 321

(56) References Cited

U.S. PATENT DOCUMENTS

| | | | | |
|---|---|---|---|---|
| 5,325,011 A | * | 6/1994 | Kahn et al. | 310/358 |
| 6,277,299 B1 | * | 8/2001 | Seyed-Bolorforosh | 310/320 |
| 6,307,299 B1 | * | 10/2001 | Suzuki et al. | 310/312 |
| 6,385,429 B1 | * | 5/2002 | Weber et al. | 310/357 |
| 6,433,463 B1 | * | 8/2002 | Lal et al. | 310/328 |

* cited by examiner

*Primary Examiner*—Helen Kwok
(74) *Attorney, Agent, or Firm*—Alston & Bird LLP

(57) ABSTRACT

A method and/or an apparatus for determining the dynamic response of a microstructure is disclosed. A piezocomposite ultrasonic transducer device formed of a piezoelectric material and a polymer material around said piezoelectric ceramic material is used to provide a pulsed bulk acoustic wave having a bandwidth of at least 20% to excite a microstructure. The microstructure is attached onto the transducer, and the pulsed bulk acoustic wave generated through the transducer in response to a pulse voltage excites the microstructure to vibrate. Meanwhile, the dynamic response of the microstructure can be monitored by a laser Doppler vibrometer, and shown by an oscilloscope.

29 Claims, 14 Drawing Sheets

METHOD AND APPARATUS FOR DETERMINING DYNAMIC RESPONSE OF MICROSTRUCTURE BY USING PULSED BROAD BANDWIDTH ULTRASONIC TRANSDUCER AS BAW HAMMER

FIELD OF THE INVENTION

The present invention relates to a method for determining a dynamic response of a microstructure, and more particularly to a method for determining a dynamic response of a microstructure by using a pulsed broad bandwidth ultrasonic transducer as a bulk acoustic wave (BAW) hammer to excite the microstructure. The present invention also relates to an apparatus for determining a dynamic response of a microstructure.

BACKGROUND OF THE INVENTION

Micro-sensors and micro-actuators are the key components in a micro electrical mechanical system (MEMS). The performance of a micro-sensor or micro-actuator correlates closely with the dynamic mechanical properties thereof. For instance, the bandwidth, resolution, and response time of some micro-sensors are determined by their mechanical resonance. The output characteristics of micro-actuators such as the force amplitude and the operating frequency thereof are also determined by their dynamic behaviors. Therefore, the testing method for evaluating the dynamic behaviors of the microstructures is very important. Several excitation and detection approaches have been developed to characterize the dynamic responses, vibration characteristics such as the natural frequencies and the mode shapes of the microstructures. Moreover, the material properties, e.g. residual stress, Young's modulus and fatigue properties, can also be determined.

The measured dynamic response of a microstructure will be affected by the excitation technique. Please refer to FIG. 1 which schematically shows a conventional excitation device which drive the microstructure through built in electrostatic electrodes. The microstructure 10 formed on a silicon substrate 11 by a semiconductor manufacturing process is an insulator cantilever, for example, made of silicon oxide. In order to allow the cantilever 10 to be excited, a conductive film 12 such as a chromium film is applied over the insulator cantilever 10. Then, a variable-frequency sinusoidal voltage could be applied between the silicon substrate 11 and the metallized line 12 leading to the cantilever 10 by way of a variable frequency oscillator 13. Accordingly, the cantilever 10 with the chromium film 12 can be electrostatically attracted toward the substrate with either voltage polarity so as to excite the mechanical motion of the cantilever 10. In this approach, an additional conductive film which does not belong to the microstructure is deposited. Therefore, this test method is a destructive one. On the other hand, the presence of the additional film 12 may influence the dynamic behavior of the original cantilever 10.

FIG. 2 schematically shows another conventional excitation device which mechanically excites a microstructure. As shown, a test chip 20 with a microstructure (not shown) is attached onto a piezotransducer 21, and a voltage 22 is applied for driving the piezotransducer 21 so as to mechanically excite the test chip 20. The piezotransducer 21 is made of PZT. The natural frequencies of a PZT disc are strongly dependent on the ratio of diameter/thickness (D/T), and a PZT disc with finite dimension has complex mode distribution in the frequency domain. Accordingly, when a PZT transducer acts as the based excitation source applied to a microstructure, it is likely to be strongly coupled with the dynamic responses of the microstructure in the frequency range of a spurious mode of the PZT transducer. In brief, a dynamic coupling effect will exist between the piezotransducer 21 and the test chip 20 so as to interfere with the dynamic responses of the microstructure.

Further refer to FIG. 3 which shows a further conventional excitation device which uses a swept-sine signal to drive a microstructure. As shown, a specimen 31 with a microstructure (not shown) is attached onto a PZT transducer 30. By providing a dynamic signal analyzer 32, a swept-sine signal is generated to drive the PZT transducer 30 and further the specimen 31. As known, a swept-sine signal generated by a dynamic signal analyzer typically has frequencies under 50 kHz so as to be suitable for a millimeter dimensional microstructure. As for a micron dimensional microstructure with higher natural frequencies, higher exciting frequencies will be required.

FIG. 4 shows a still further conventional excitation device which uses acoustic waves to excite a microstructure. As shown, a small loudspeaker 41 is mounted above a cantilever 40 to be excited. By providing a power for the loudspeaker 41, the acoustic waves 43 propagate via the air to the cantilever 40, thereby forcing the cantilever 40 to vibrate. In this approach, the acoustic waves 43 have to be transmitted to the cantilever 40 via air so that the cantilever 40 cannot be excited in a vacuum environment where micron dimensional microstructures are possibly located.

SUMMARY OF THE INVENTION

Therefore, an object of the present invention is to provide a method and/or apparatus for determining a dynamic response of a microstructure, in which no additional film is deposited on the microstructure to be excited.

Another object of the present invention is to provide a method and/or apparatus for determining a dynamic response of a microstructure, in which the dynamic coupling effect between the transducer and the microstructure is minimized.

A further object of the present invention is to provide a method and/or apparatus for determining a dynamic response of a microstructure, which can be used for a micron dimensional microstructure.

A still further object of the present invention is to provide a method and/or apparatus for determining a dynamic response of a microstructure, which can be operated in a vacuum environment.

According to a first aspect of the present invention, a method for determining a dynamic response of a microstructure includes steps of attaching the microstructure to an ultrasonic transducer device; providing a pulse voltage to excite the ultrasonic transducer device so as to generate a pulsed bulk acoustic wave which has a bandwidth of at least 20%; and utilizing free vibration of the microstructure resulting from the pulsed bulk acoustic wave to determine the dynamic response of the microstructure. Preferably, the bandwidth is no less than 30%.

The microstructure is preferably attached to the ultrasonic transducer device by adhering a substrate of the microstructure to the ultrasonic transducer device in a nondestructive manner. For example, the substrate is adhered to the ultrasonic transducer device by wax or a sticky tape.

Preferably, the ultrasonic transducer device is a piezocomposite ultrasonic transducer. More preferably, the ultrasonic transducer device includes a piezoelectric portion and a polymer portion around the piezoelectric portion.

A second aspect of the present invention relates to a method for determining a dynamic response of a microstructure includes steps of attaching the microstructure to a piezocomposite ultrasonic transducer device formed of a piezoelectric material and a polymer material around said piezoelectric ceramic material; providing a pulse voltage for the piezocomposite layer to excite the ultrasonic transducer device so as to generate a pulsed bulk acoustic wave; and utilizing free vibration of the microstructure resulting from the pulsed bulk acoustic wave to determine the dynamic response of the microstructure.

Preferably, the piezoelectric material is PZT, and the polymer is epoxy resin or silicone.

Preferably, the pulsed bulk acoustic wave has a bandwidth of at least 20%, and more preferably, at least 30%, and a central frequency of hundreds of kHz to tens of MHz.

A third aspect of the present invention relates to an apparatus for determining a dynamic response of a microstructure includes a pulse generator for providing a pulse voltage; a piezocomposite ultrasonic transducer device including a plurality of piezoelectric ceramic rods filled with a polymer therebetween, and connected to said pulse generator for generating a pulsed bulk acoustic wave in response to said pulse voltage to vibrate said microstructure secured thereon; a detecting device positioned to detect the vibrating microstructure for determining the dynamic response of the microstructure.

Preferably, the piezocomposite ultrasonic transducer is divided into three layers, i.e. piezocomposite layers, matching layers, and a backing layer. The matching layer is formed of epoxy resin for acoustic impedance matching; the piezocomposite layer consists of a PZT rod matrix filled with epoxy resin for emitting the pulsed bulk acoustic wave; and the backing layer is formed of epoxy resin or silicone for damping the acoustic wave from the rear surface of piezocomposit layer. If necessary, matching layers and/or piezocomposite layers can be repetitively provided. Alternatively, matching layers and/or the backing layer can be omitted. Further, piezoelectric layers such as PZT layers can also be used along with the matching and backing layers to achieve the purpose of the present invention.

Preferably, the detecting device includes a laser Doppler vibrometer positioned above the microstructure for monitoring the dynamic response of the vibrating microstructure as a photo-signal; a photoelectric converter electrically connected to the laser Doppler vibrometer for converting the photo-signal into an electric signal; and an oscilloscope electrically connected to the photoelectric converter for displaying the dynamic response in response to the electric signal.

In an embodiment, the photoelectric converter is a charge coupled device (CCD).

The oscilloscope and the pulse generator can be separate devices interconnected to each other, or the oscilloscope can include therein the pulse generator.

For a microstructure used in a vacuum environment, a vacuum chamber is further provided for accommodating therein the ultrasonic transducer device and the microstructure to perform the determination of the dynamic response.

The method and/or apparatus according to the present invention are suitable for determining a dynamic response of a torsional micro-mirror or a micro-cantilever or any other similar microstructure.

BRIEF DESCRIPTION OF THE DRAWINGS

The present invention may best be understood through the following description with reference to the accompanying drawings, in which.

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

Figure 1:
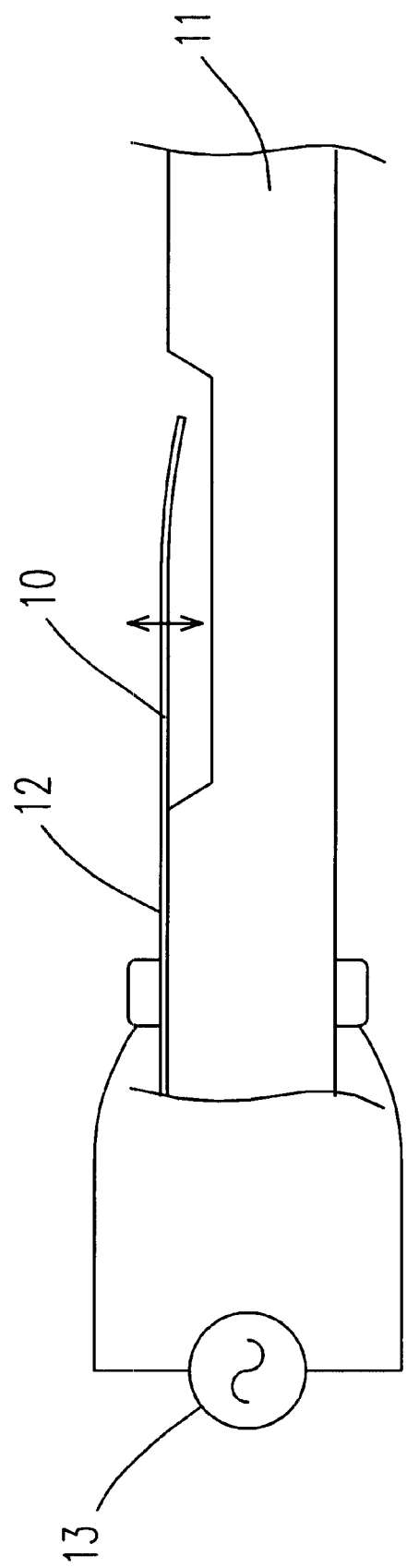
FIG. 1 is a schematic diagram showing a first conventional excitation device which drive the microstructure through built in electrostatic electrodes.
Figure 2:
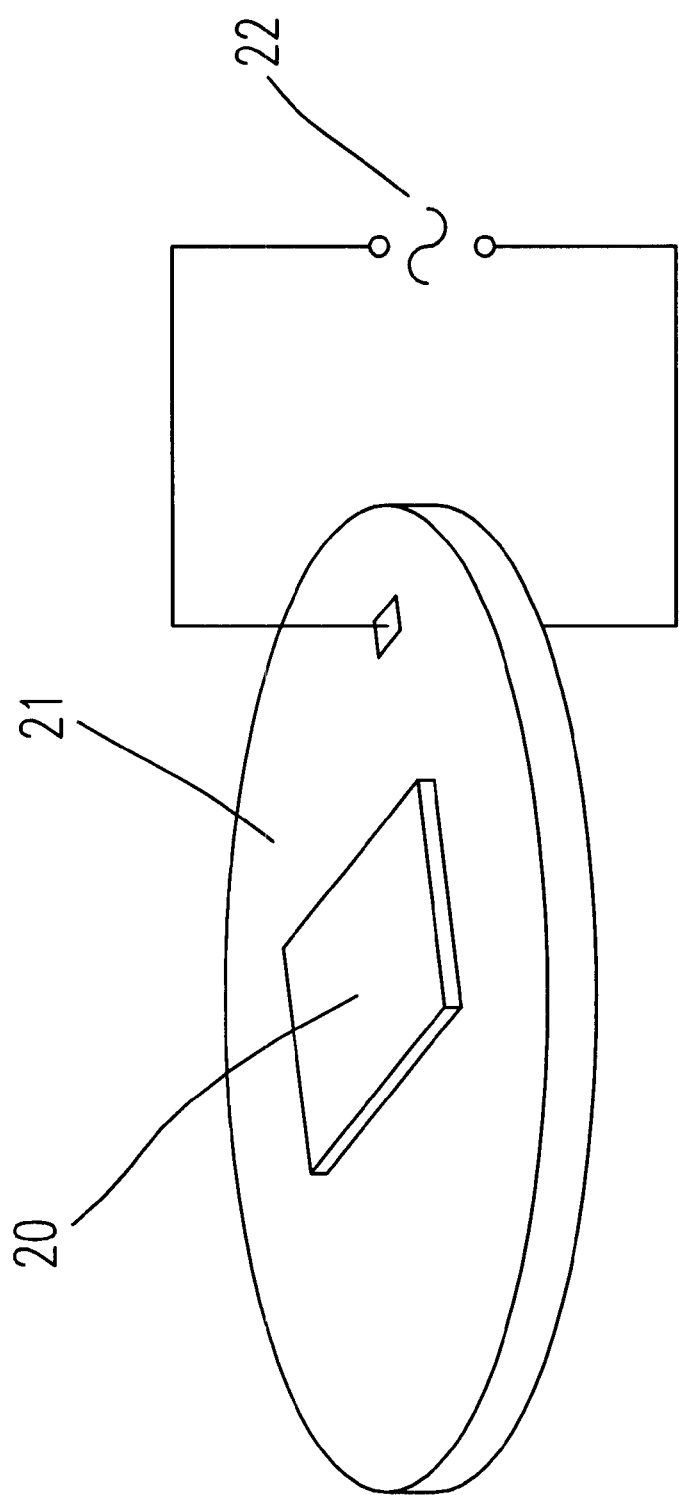
FIG. 2 is schematic diagram showing a second conventional excitation device which mechanically excites a microstructure.
Figure 3:
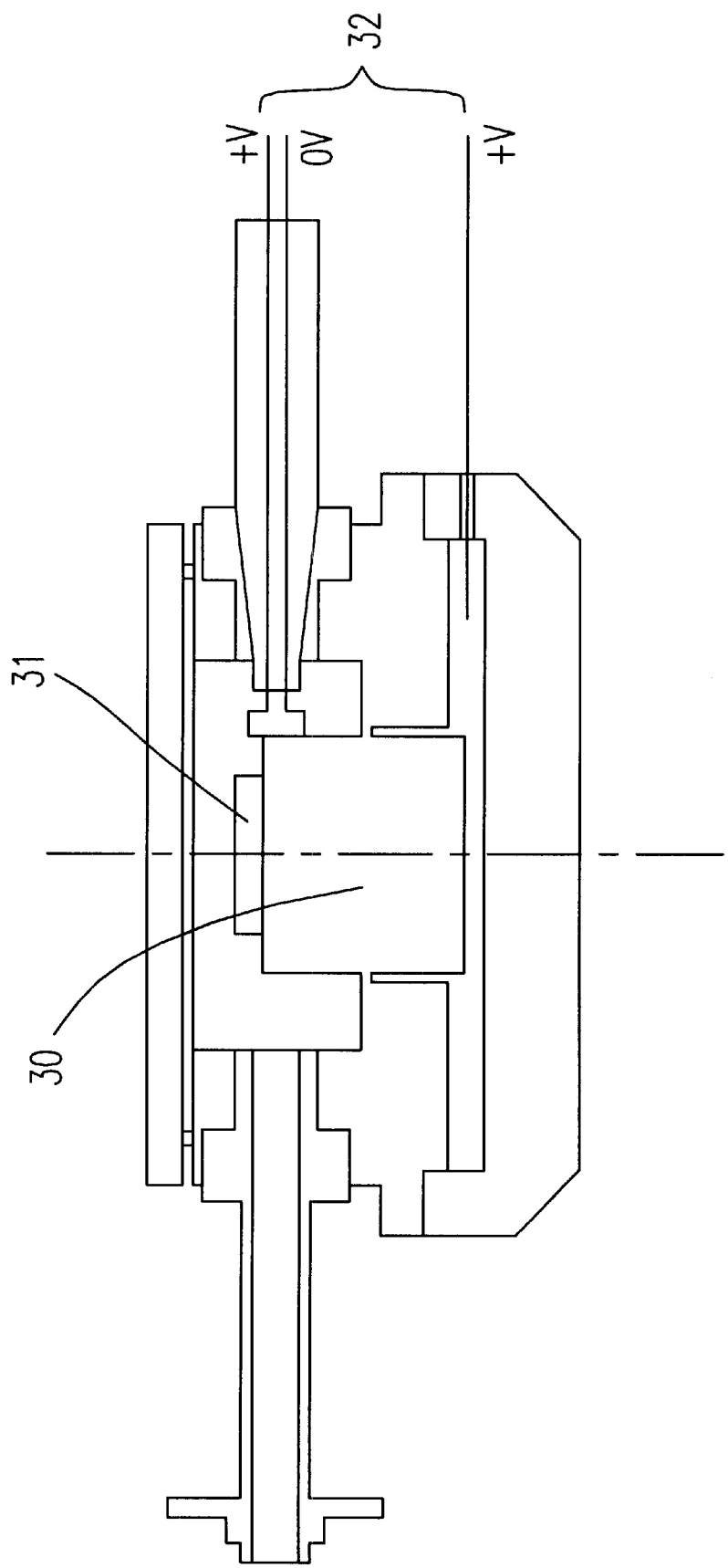
FIG. 3 is schematic diagram showing a third conventional excitation device which uses a swept-sine signal to drive a microstructure.
Figure 4:
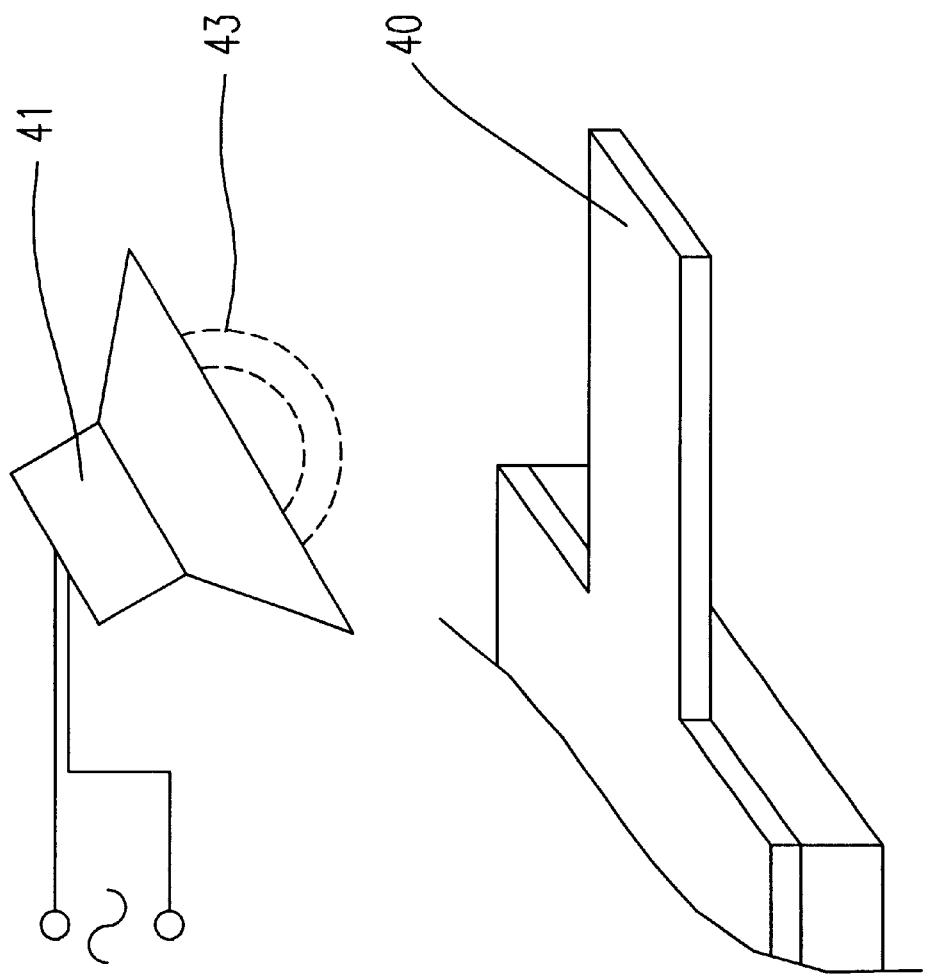
FIG. 4 is schematic diagram showing a fourth conventional excitation device which uses acoustic waves to excite a microstructure.
Figure 5A:
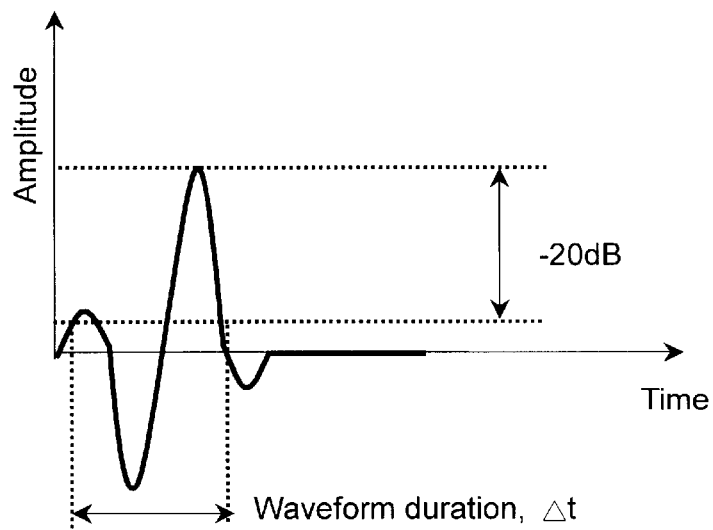
FIG. 5A is a theoretical amplitude vs. time plot of a pulsed bulk acoustic wave.
Figure 5B:
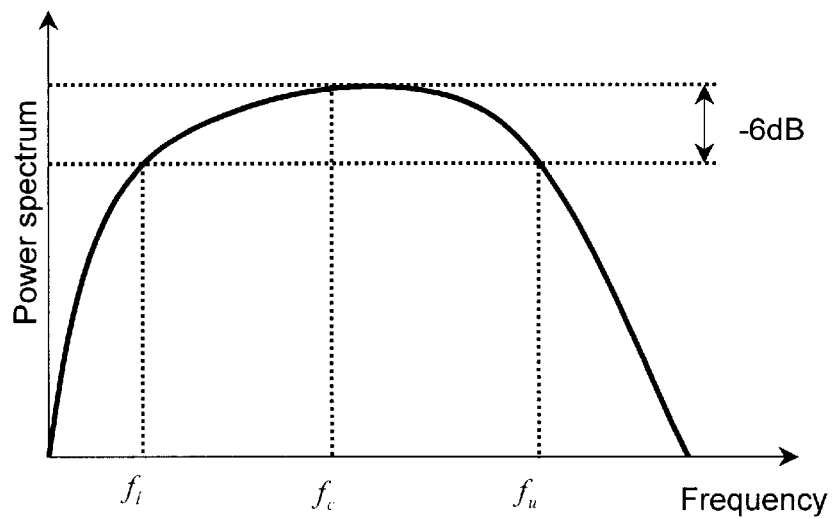
FIG. 5B is a theoretical power spectrum vs. frequency plot of the pulsed bulk acoustic wave of FIG. 5A.

As understood, an impulse with a specific amplitude A and duration Δt can excite all the vibration modes of a structure within a certain frequency range. For an impulse, the effective frequency is inversely proportional to the duration Δt. For higher natural frequencies of a microstructure, it is necessary to induce a pulse with a shorter Δt to raise the testing frequency range. In the present invention, the broad bandwidth ultrasonic transducer is used to generate bulk acoustic wave (BAW). The BAW, acting as an impact hammer, is employed to generate an impulse excitation to excite the microstructures during the vibration test. According to the ASTM (American Society for Testing and Materials) code E1065, the waveform duration Δt is defined as the −20 dB level amplitude of peak. In other words, FIGS. 5A and 5B show theoretical frequency- and time-dependent responses of an impulse, respectively, and illustrates the definition of parameters of the impulse. In FIGS. 5A and 5B, the symbol $f_c$ indicates the central frequency in the frequency response of the waveform, and is expressed as $$f_c = (f_u + f_l)/2 \qquad (1)$$

wherein the symbols $f_u$ and $f_l$ indicate upper and lower frequencies of a power spectrum range defined by a power spectrum drop of 6 dB from its peak point, as shown in FIG. 5B. The bandwidth BW of the transducer is defined as $$BW = ((f_u - f_l)/f_c) \times 100 \qquad (2).$$

Hence, the natural modes of the microstructure within the BW range of the excitation shown in FIG. 5B will be excited. In other words, the $f_c$ and the BW of an excitation can be adjusted by changing the transducer. On the other hand, in order to minimize or even eliminated the dynamic coupling effect between the transducer and the microstructure, the ripple originated from the radial natural mode of the transducer should be damped immediately. This purpose can be achieved by employing a transducer of a broad bandwidth with a constant load. According to the inventors' research, a bandwidth of at least 20%, preferably, at least 30%, along with a central frequency of 50 kHz to 10 MHz, is especially suitable for determining a dynamic response of a microstructure.

Figure 5C:
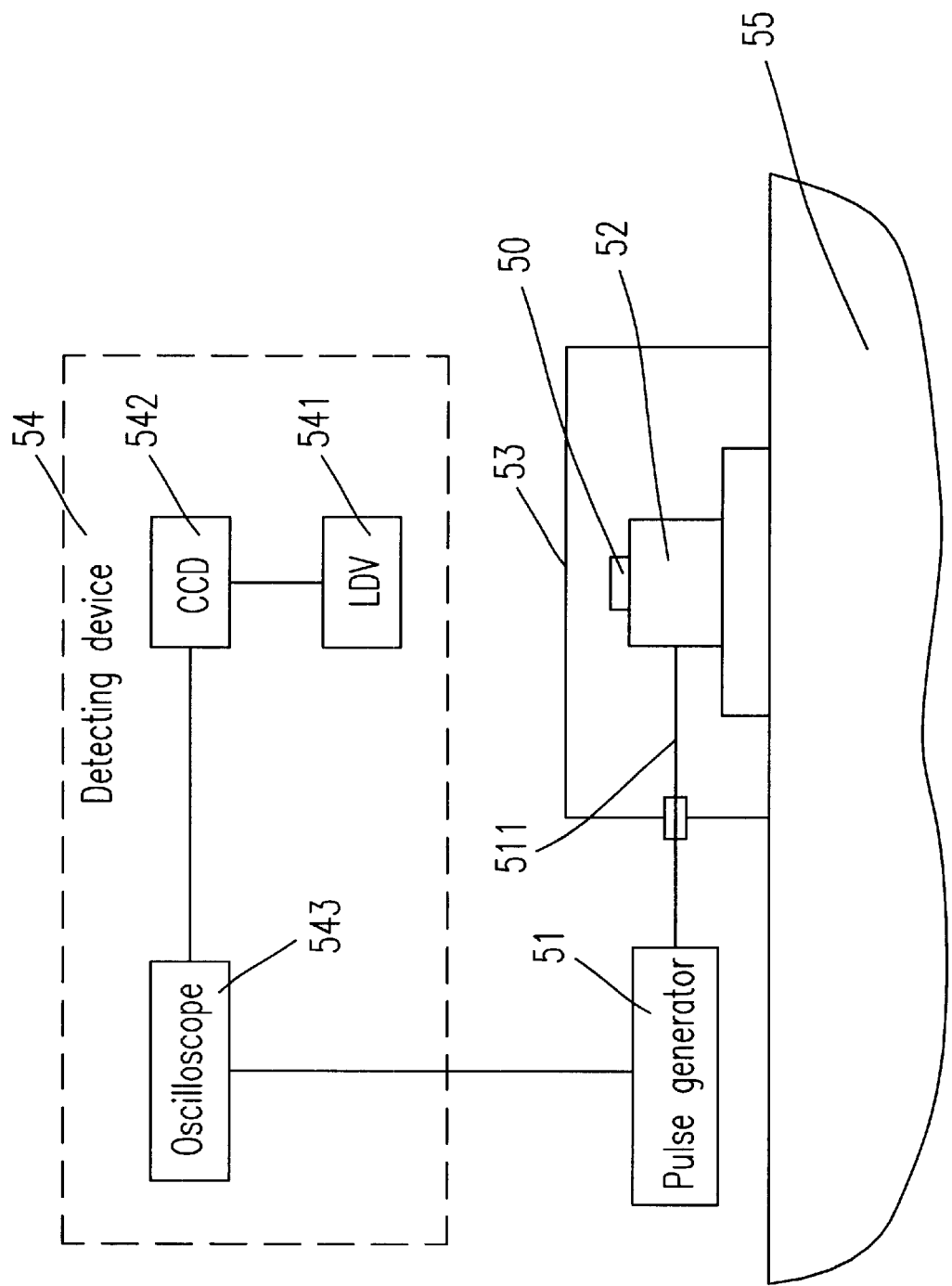
FIG. 5C is a schematic diagram showing a preferred embodiment of an apparatus for determining a dynamic response of a microstructure according to the present invention.
Figure 5D:
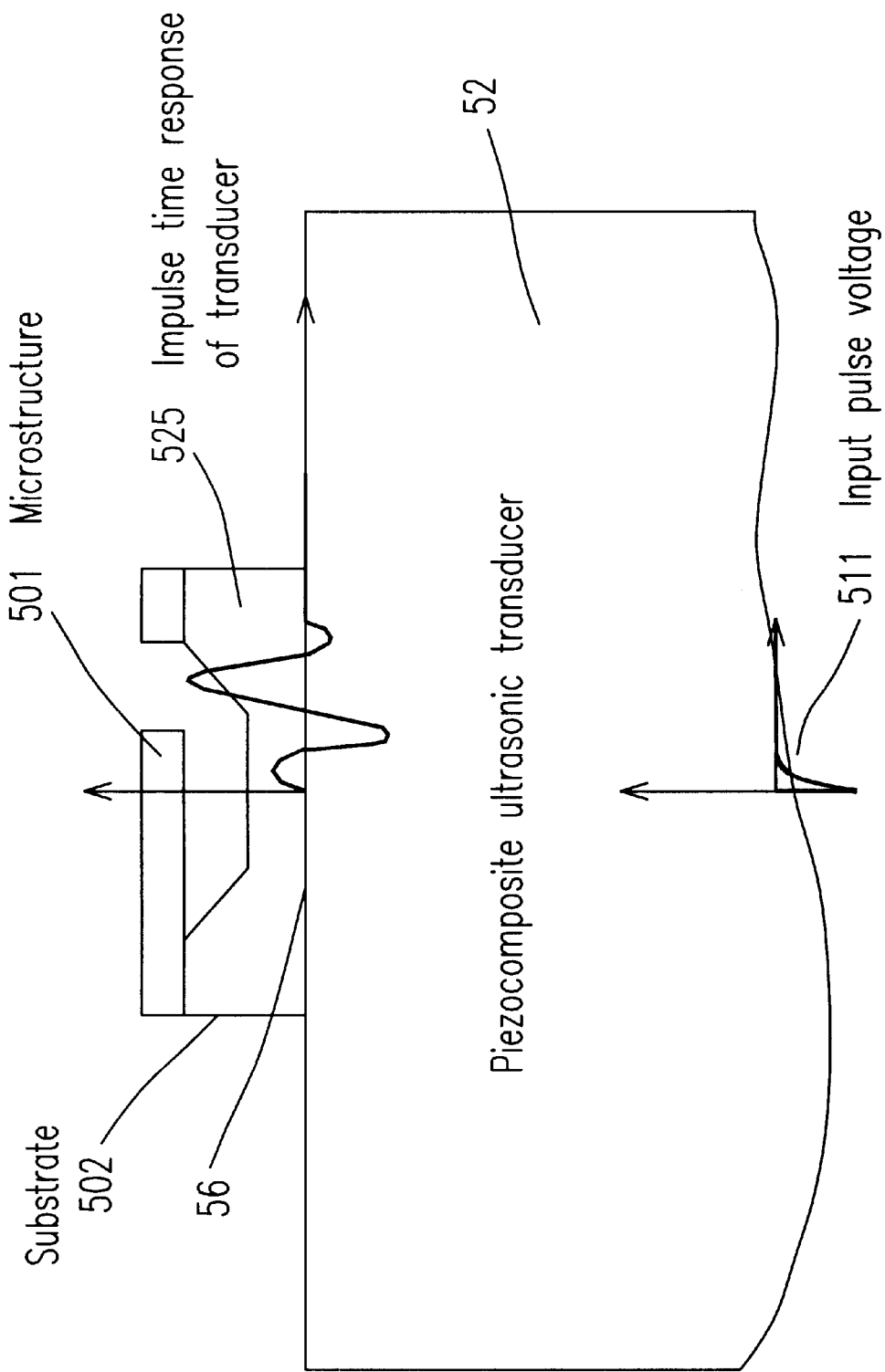
FIG. 5D is a schematic diagram showing that a pulsed bulk acoustic wave is generated by the transducer of FIG. 5C in response to an input pulse voltage for exciting the microstructure.

Please refer to FIGS. 5C and 5D which schematically shows a preferred embodiment of an apparatus for determining a dynamic response of a microstructure according to the present invention. As shown in FIG. 5C, the apparatus includes a pulse generator 51, an ultrasonic transducer device 52, a vacuum chamber 53 and a detecting device 54. Referring to FIG. 5D, a specimen 50 with a microstructure 501 formed on a substrate 502 is attached onto the top surface of the ultrasonic transducer device 52 to be monitored. The substrate 502 is adhered to the ultrasonic transducer device 52 in a nondestructive manner, e.g. by wax or a sticky tape 56. The ultrasonic transducer device 52 is placed on a vibration isolated table 55. If necessary, the ultrasonic transducer device 52 and the specimen 50 are accommodated in the vacuum chamber 53 to create a vacuum environment.

A pulse voltage 511 is repetitively provided for the ultrasonic transducer device 52 by the pulse generator 51. For example, the pulse is 175 volt in amplitude, 0.23 microseconds in width, and 1 kHz in repetition rate. A schematic waveform of the input pulse voltage 511 is shown in FIG. 5B. In response to the pulse voltage 511, the ultrasonic transducer device 52 is excited to generate a pulsed bulk acoustic wave 525 (FIG. 5D). The pulsed bulk acoustic wave 525 excites the microstructure 501 to vibrate. After a transient response of the transducer 52, free vibration of the microstructure 501 can be realized for determining dynamic responses of the microstructure.

Figure 6A:
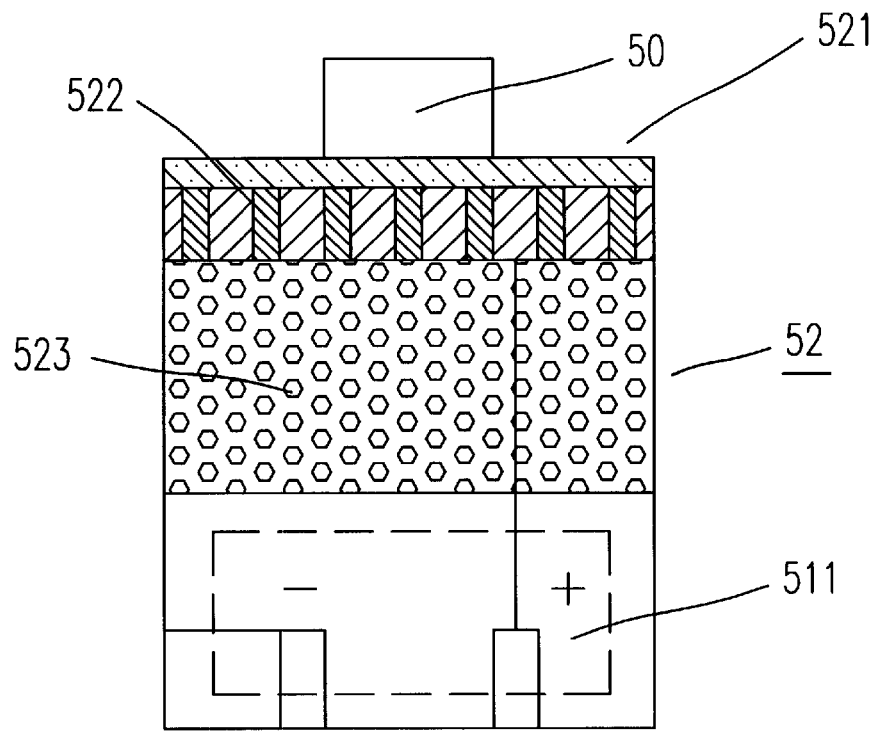
FIG. 6A is a schematic diagram showing a preferred embodiment of a transducer suitable for use in the apparatus of FIG. 5A.
Figure 6B:
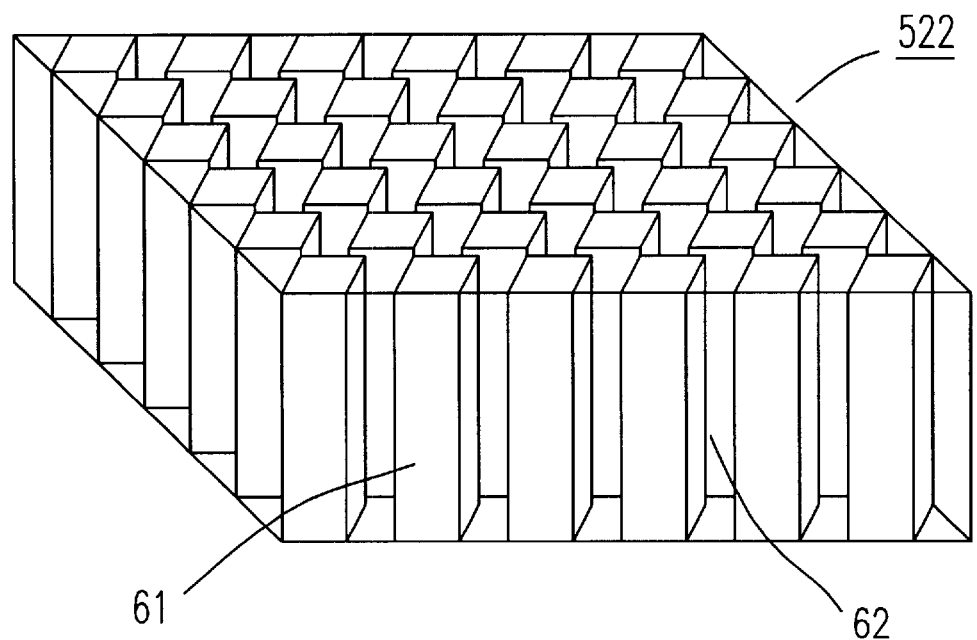
FIG. 6B is a schematic diagram showing the piezocomposite layer portion of the transducer of FIG. 6A.

The ultrasonic transducer device 52 has a tri-layer structure, as shown in FIG. 6A. The upper layer 521 in contact with the specimen 50 is a matching layer for acoustic impedance matching. The matching layer 521 can be made of epoxy resin. Then, a piezocomposite layer 522 including a PZT-rod matrix 61 filled with polymer 62 (FIG. 6B) is provided for generating the pulsed bulk acoustic wave. Further, a backing layer 523 formed of epoxy resin or silicone with powder impurity is provided for damping the acoustic wave from the rear surface of piezocomposite layer. By using such a piezocomposite ultrasonic transducer, the requirements on the bandwidth, i.e. 20% up, of the pulsed bulk acoustic wave for exciting a microstructure can be complied with. Please refer to FIGS. 7A–7D which show experimental results demonstrating the feasibility of the present transducer.

Figure 7A:
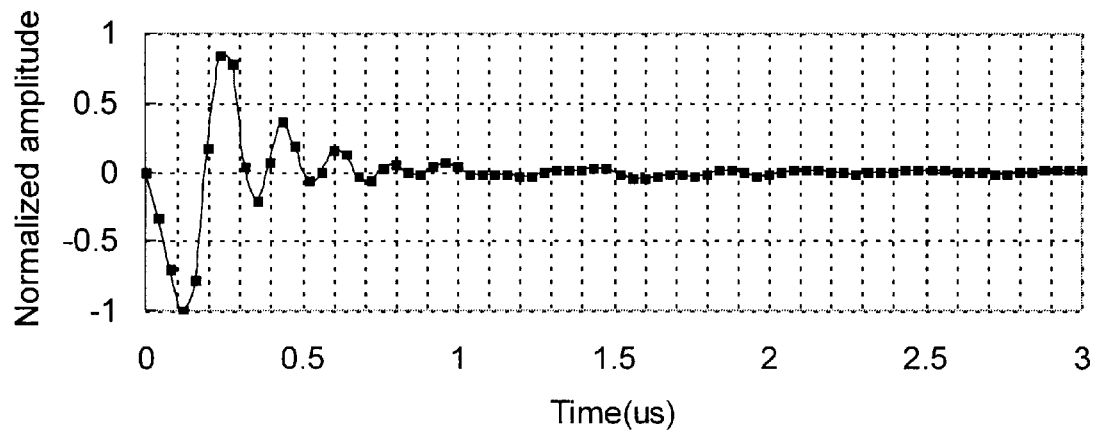
FIG. 7A is an amplitude vs. time plot of a pulsed bulk acoustic wave generated by the transducer of FIG. 6.
Figure 7B:
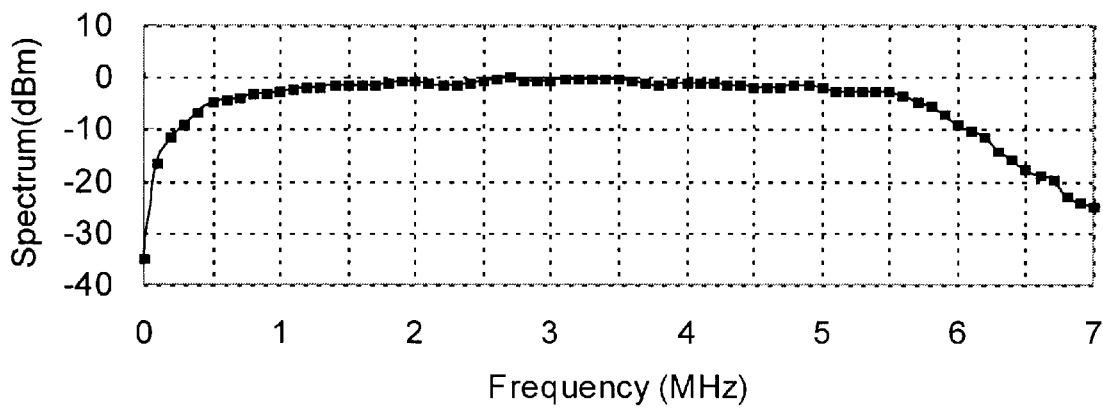
FIG. 7B is a power spectrum vs. frequency plot of a pulsed bulk acoustic wave generated by the transducer of FIG. 6.
Figure 7C:
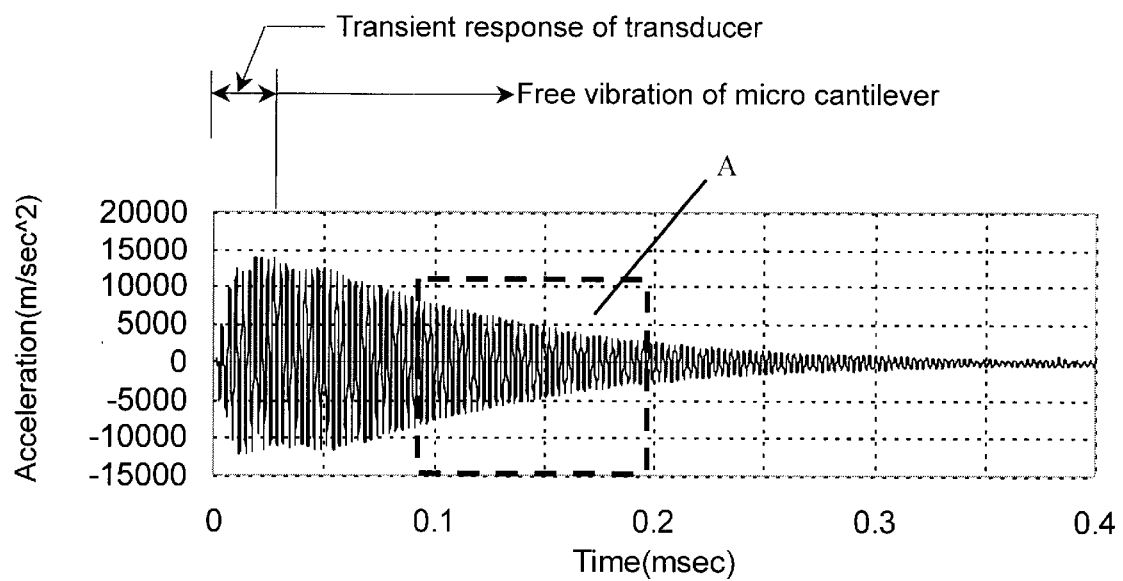
FIG. 7C is an acceleration vs. time plot of the combination of the transducer of FIG. 6 and a micro-cantilever to be excited.
Figure 7D:
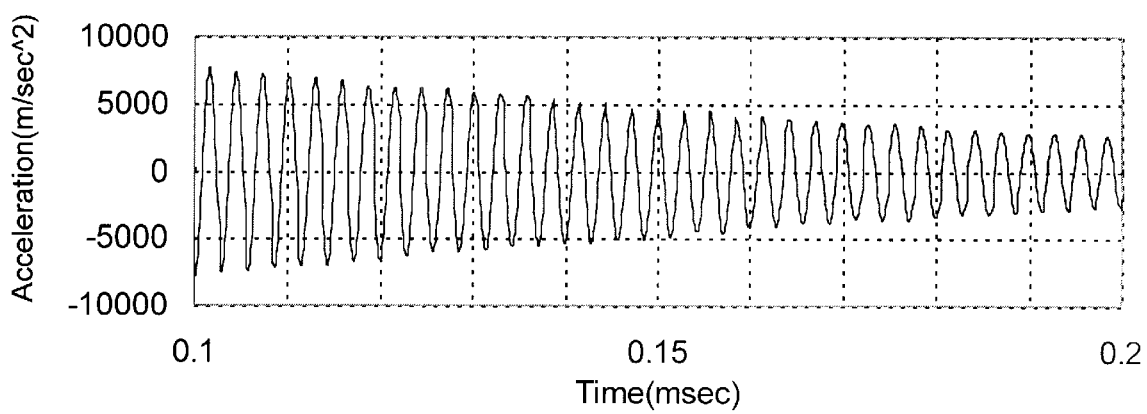
FIG. 7D is a partially enlarged view of the plot of FIG. 7C.

FIGS. 7A and 7B show the pulsed bulk acoustic wave of a bandwidth over 100% with a central frequency up to 3 MHz, which is comparable to that of FIGS. 5A and 5B. FIG. 7C shows the measured impulse time response of a micro-cantilever of 1.11 μm thick, 6 μm wide and 50 μm long. FIG. 7D is a zoom-in view of the range A of the plot of FIG. 7C. It is apparent from the plots that the micro-cantilever has free vibration after a few cycles of excitation according to the present invention.

Referring to FIG. 5C again, after the microstructure 501 is excited to vibrate by the pulse bulk acoustic wave, various dynamic responses including the resonant frequency, mode shape and modal damping of the microstructure can be measured by the detecting device 54. The detecting device 54 includes a laser Doppler vibrometer (LDV) 541, a charge coupled device (CCD) 542 and an oscilloscope 543. The LDV 541 is positioned above the microstructure for monitoring the dynamic responses of the vibrating microstructure as a photo-signal. The CCD 542 converts the photo-signal into an electric signal. Then, the dynamic responses are displayed by the oscilloscope 543.

In the embodiment shown in FIG. 5C, the pulse generator 51 broadly indicates any device capable of generating pulse voltages suitable for the use of the present invention. For example, it can be an independent device. Alternative, it can be a part of the oscilloscope 543, or replaced by a function generator together with a power amplifier.

In order to demonstrate the performance of the present apparatus and method, a few experiments are made as follows. A micromachined cantilever having an undamped natural frequency $$f_n = (1/2\pi)(\lambda_n)^2 (Eh^2/12 \rho L^4)^{1/2} \qquad (3),$$

is used as the test microstructure, wherein E, ρ, L and h are Young's modulus, density, length and thickness of said cantilever, respectively, $\lambda_n$ is an eigen value of a problem and is given by a solution to cos $h(\lambda_n)\cos(\lambda_n)+1=0$, and n is an integer indicating the $n^{th}$ natural mode. The mode shape $V_n(x)$ of the beam at bending modes is expressed as $$V_n(x) = A_n[\sin(\lambda_n x) - \sin h(\lambda_n x) - C_n \cos(\lambda_n x) + C_n \cos h(\lambda_n x)]$$

$$A_n = (\sin h\lambda_n - \sin \lambda_n)/2(\cos h\lambda_n + \cos \lambda_n)$$

$$C_n = (\cos h\lambda_n + \cos \lambda_n)/\sin h\lambda_n - \sin \lambda_n \qquad (4).$$

Figure 8A:
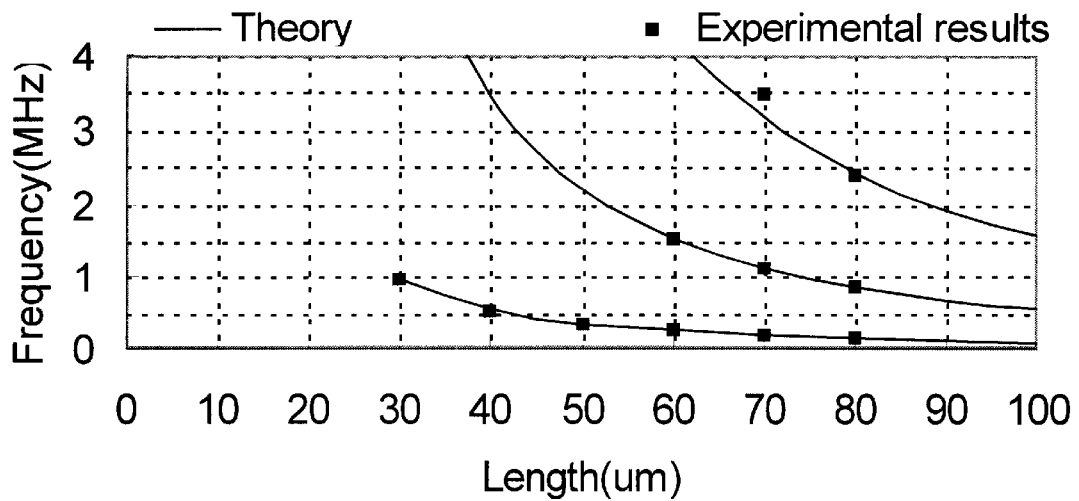
FIG. 8A is a frequency vs. cantilever length plot for showing a dynamic response of a micro-cantilever excited by the present method and apparatus.
Figure 8B:
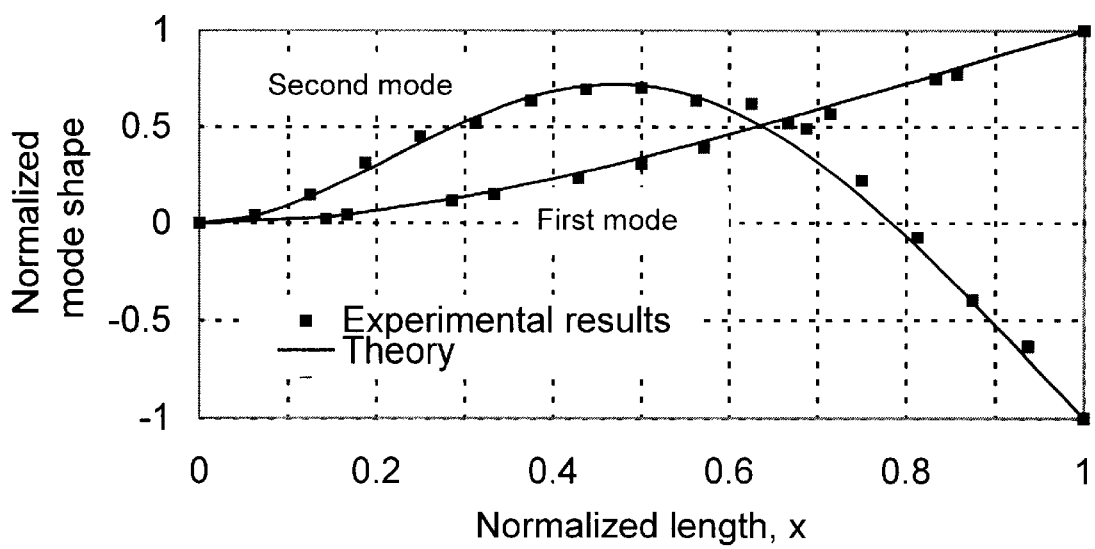
FIG. 8B is a mode shape vs. length plot for showing another dynamic response of a micro-cantilever excited by the present method and apparatus.

The free vibration of a microstructure in both time and frequency domains is measured after the excitation according to the present method. To verify the validation of the present method, the comparison between the measured resonant frequencies and the predicted ones is shown in FIG. 8A. The solid line was predicted by the equation (3) based on the density and Young's modulus of microstructures known previously. Apparently, the experimental results agree well with the predicted ones. The deviation between the experimental and analytical results was 2% to 6%. On the other hand, the variation of the natural frequency with the beam in different lengths can also be used to determine the Young's modulus of a thin film. In this regard, the Young's modulus of the microbeam is obtained after curve fitting the data points in FIG. 8A according to the equation (3). The mode shape of the microstructure can also be determined after measuring the spectrum at different position of the beam. Comparison of the measured and predicted results is shown in FIG. 8B. The data points represent the measured results and the solid lines were predicted by the equation (4).

Figure 9:
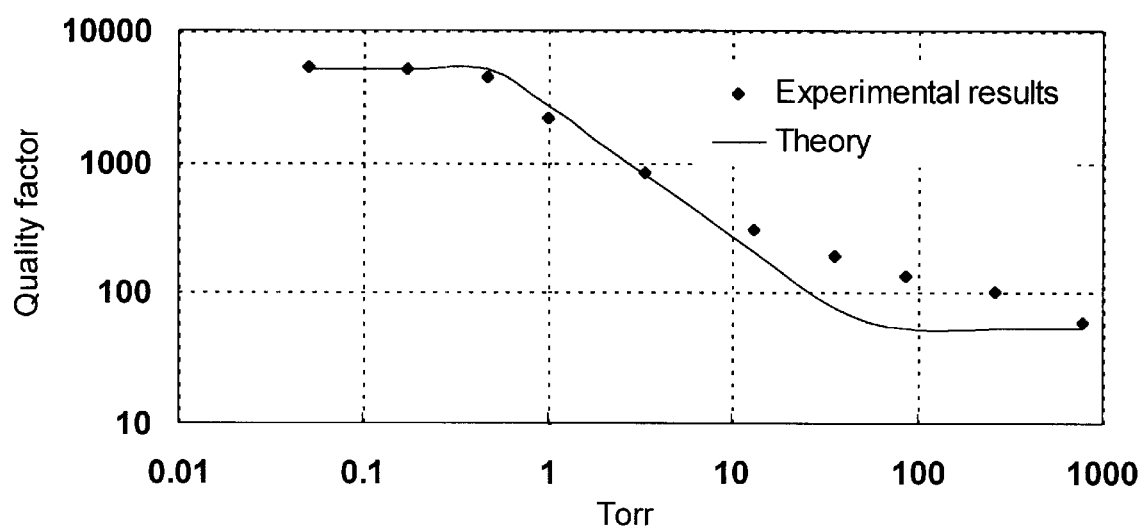
FIG. 9 is a quality factor vs. pressure plot for showing a further dynamic response of a micro-cantilever excited by the present method and apparatus.

The equivalent modal damping (or quality factor Q) of the microbeam due to the air effect can be divided into three regions. In the near vacuum region, the intrinsic Q is independent of pressure and must be determined empirically. Under the atomosphere pressure region, gas is regared as viscous fluid. Therefore, the relation of the Q and the dimension of the microbeam is determined by the Stoke's Law $$Q=(h/L)^2[b(E\rho)^{1/2}/24\,\mu] \quad (5),$$

Where $\mu$ is the viscousity of the air and b is the width of the microbeam. If the microstructure is operating under low pressure, the relation between the quality factor and the dimension of the microbeam becomes $$Q=93(h/L)^2[(E\rho)^{1/2}/P] \quad (6),$$

Where P is the pressure of the air. In FIG. 9, the quality factor of the first bending mode for a L=60 $\mu$m beam under various air pressures was also measured through the present method. The experimental results agree well with the analytical results predicted by the equations (5) and (6).

Figure 10A:
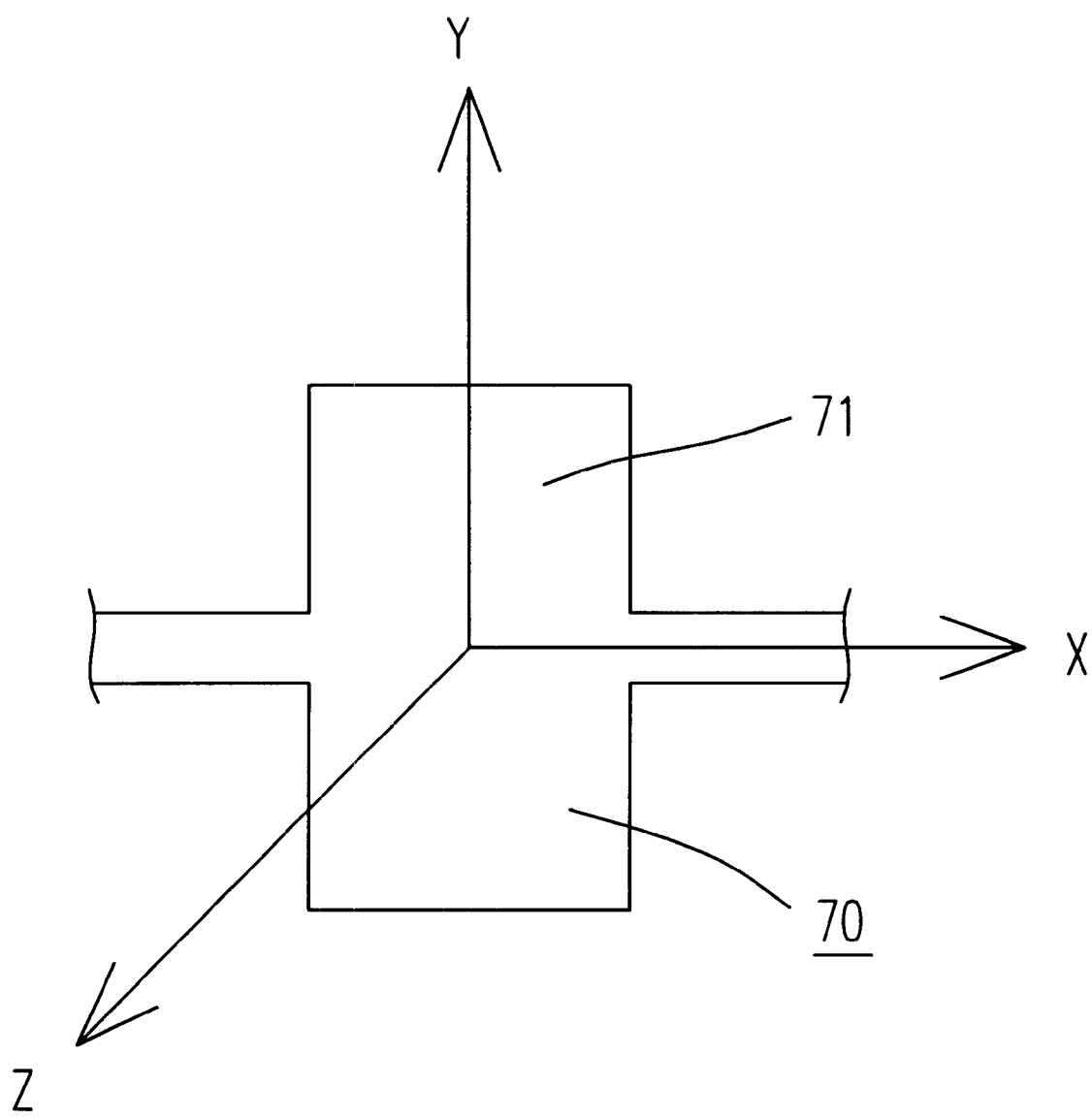
FIG. 10A is a schematic diagram showing a micro-mirror to be excited according to the present invention.
Figure 10B:
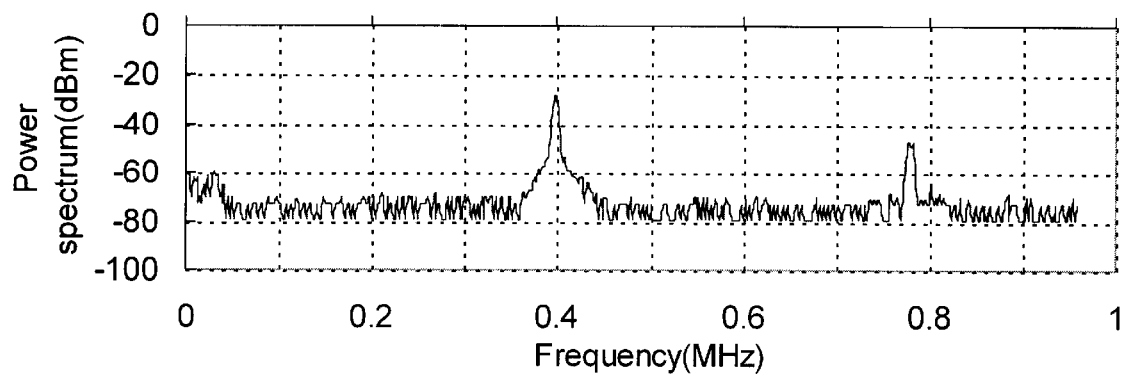
FIG. 10B is a power spectrum vs. frequency plot of the micro-mirror of FIG. 10A when the laser spot is on the center of the plate.
Figure 10C:
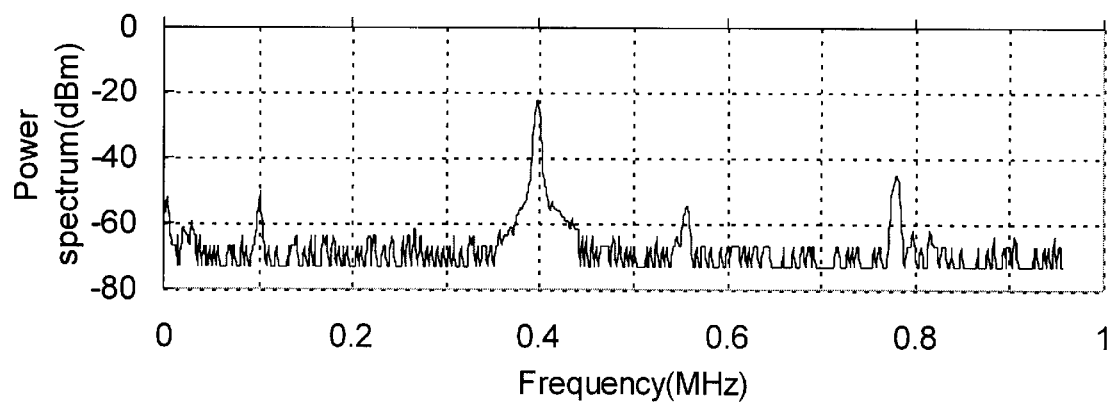
FIG. 10C is a power spectrum vs. frequency plot of the micro-mirror of FIG. 10A when the laser spot is on the side of the plate.

The present invention is applicable to test various microstructures. The time response and frequency spectrum of a torsional mirror of FIG. 10A after excited according to the present invention is demonstrated in FIGS. 10B~10C. As shown in FIG. 10A, the plate 71 of the torsional mirror 70 will pitch about its suspension (x-axis), roll about the y-axis, and move transversely in the z-axis when excited. Although the dynamic response of the plate 71 may be complex, the present method will easily distinguish the different vibration modes of the plate by changing the detecting position of the laser spot. The frequency spectrums in FIGS. 10B and 10C were measured at a central and an end positions of the plate 71, respectively. It is obtained that the vibration modes at $f_n$=100 kHz and 560 kHz are vanished in FIG. 10B. From the detecting position of the laser spot, it is deduced that the first torsional mode of the plate is approximately at $f_n$=100 kHz. The deviation between the experimental and FEM analysis results was 4%.

According to the present invention, a novel method and/or apparatus are used to determine the dynamic response of a microstructure by using a pulsed broad bandwidth ultrasonic transducer as a bulk acoustic wave (BAW) hammer. Experimental results demonstrated that the present method is a fast and promising approach for characterizing the dynamic behaviors of the microstructure. Further, the present invention has the following advantages. The sample preparation is very easy since it is not necessary to deposit any additional film for thermal or electrical purposes. In this regard, the experimental results are more accurate since there is no additional thin film to influence the dynamic behavior of the test sample. Moreover, there is no uncertain side effect such as thermal and acoustic coupling. Further, the present apparatus is so simple that it has the potential to perform on-line tests for batch production.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for determining a dynamic response of a microstructure, comprising the steps of:
    attaching said microstructure to an ultrasonic transducer device;
    providing a pulse voltage to excite said ultrasonic transducer device so as to generate a pulsed bulk acoustic wave which has a bandwidth of at least 20%; and
    detecting free vibration of said microstructure resulting from said pulsed bulk acoustic wave to determine said dynamic response of said microstructure.

2. The method according to claim 1 wherein said microstructure is attached to said ultrasonic transducer device by adhering a substrate of said microstructure to said ultrasonic transducer device in a nondestructive manner.

3. The method according to claim 2 wherein said substrate is adhered to said ultrasonic transducer device by wax.

4. The method according to claim 2 wherein said substrate is adhered to said ultrasonic transducer device by a sticky tape.

5. The method according to claim 1 wherein said ultrasonic transducer device sequentially includes a piezoelectric layer, a matching layer, and a backing layer below said microstructure.

6. The method according to claim 1 wherein said ultrasonic transducer device includes at least one piezocomposite layer below said microstructure.

7. The method according to claim 6 wherein said ultrasonic transducer device further includes at least one matching layer and a backing layer on opposite sides of said piezocomposite layer.

8. The method according to claim 1 wherein a central frequency of said pulsed bulk acoustic wave lies between 50 kHz and 10 MHz for determining said dynamic response of said microstructure.

9. A method for determining a dynamic response of a microstructure, comprising the steps of:
    attaching said microstructure to a piezocomposite ultrasonic transducer device formed of a piezoelectric material and a polymer material around said piezoelectric material;
    providing a pulse voltage to excite said ultrasonic transducer device so as to generate a pulsed bulk acoustic wave; and
    detecting free vibration of said microstructure resulting from said pulsed bulk acoustic wave to determine said dynamic response of said microstructure.

10. The method according to claim 9 wherein said piezoelectric material is PZT.

11. The method according to claim 9 wherein said polymer material is one selected from a group consisting of epoxy resin and silicone.

12. The method according to claim 9 wherein said piezocomposite ultrasonic transducer device includes a plurality of PZT rods filled with epoxy resin therearound.

13. The method according to claim 9 wherein said piezocomposite ultrasonic transducer device includes a plurality of PZT rods filled with silicone therearound.

14. The method according to claim 9 wherein a bandwidth of said pulsed bulk acoustic wave is at least 20%.

15. The method according to claim 9 wherein a central frequency of said pulsed bulk acoustic wave lies between 50 kHz and 10 MHz for determining said dynamic response of said microstructure.

16. An apparatus for determining a dynamic response of a microstructure, comprising:

a pulse generator for providing a pulse voltage;

a piezocomposite ultrasonic transducer device including a plurality of piezoelectric ceramic rods filled with a polymer therebetween, and connected to said pulse generator for generating a pulsed bulk acoustic wave in response to said pulse voltage to vibrate said microstructure secured thereon;

a detecting device positioned to detect said vibrating microstructure for determining said dynamic response of said microstructure.

17. The apparatus according to claim 16 wherein said piezoelectric ceramic rods are PZT rods.

18. The apparatus according to claim 16 wherein said polymer is one selected from a group consisting of epoxy resin and silicone.

19. The apparatus according to claim 16 wherein said piezocomposite ultrasonic transducer device further includes a matching layer between said piezoelectric ceramic rods and said microstructure for acoustic impedance matching.

20. The apparatus according to claim 19 wherein said matching layer is formed of epoxy resin.

21. The apparatus according to claim 19 wherein said piezocomposite ultrasonic transducer device further includes a backing layer opposite to said matching layer for damping said pulsed bulk acoustic wave.

22. The apparatus according to claim 21 wherein said backing layer is formed of a material selected from a group consisting of epoxy resin or silicone.

23. The apparatus according to claim 21 wherein said backing layer is formed of silicone with powder impurity.

24. The method according to claim 16 wherein a bandwidth of said pulsed bulk acoustic wave is at least 20%.

25. The method according to claim 16 wherein a central frequency of said pulsed bulk acoustic wave lies between 50 kHz and 10 MHz for determining said dynamic response of a microstructure.

26. The apparatus according to claim 16 wherein said detecting device includes:

a laser Doppler vibrometer positioned above said microstructure for monitoring said dynamic response of said vibrating microstructure as a photo-signal;

a photoelectric converter electrically connected to said laser Doppler vibrometer for converting said photo-signal into an electric signal; and an oscilloscope electrically connected to said photoelectric converter for displaying said dynamic response in response to said electric signal.

27. The apparatus according to claim 26 wherein said photoelectric converter is a charge coupled device.

28. The apparatus according to claim 26 wherein said oscilloscope includes therein said pulse generator.

29. The apparatus according to claim 16 further comprising a vacuum chamber for accommodating therein said ultrasonic transducer device and said microstructure.

* * * * *